United States Patent
Weil, Sr. et al.

(10) Patent No.: US 6,811,552 B2
(45) Date of Patent: Nov. 2, 2004

(54) DEVICE FOR SECURING BITS OF BONE TOGETHER

(75) Inventors: Lowell Scott Weil, Sr., Des Plaines, IL (US); Anne Céline Godest, Lyons (FR)

(73) Assignee: DePuy France, Saint-Priest (FR)

( * ) Notice: Subject to any disclaimer, the term of this patent is extended or adjusted under 35 U.S.C. 154(b) by 0 days.

(21) Appl. No.: 10/184,895

(22) Filed: Jul. 1, 2002

(65) Prior Publication Data

US 2003/0040751 A1 Feb. 27, 2003

Related U.S. Application Data

(60) Provisional application No. 60/301,858, filed on Jul. 2, 2001.

(51) Int. Cl.[7] .............................................. H61B 17/58
(52) U.S. Cl. ........................... 606/73; 606/72; 411/307; 411/416
(58) Field of Search .............................. 606/59, 60, 65, 606/72, 73; 411/2, 3, 5, 263, 307, 416, 418, 420

(56) References Cited

U.S. PATENT DOCUMENTS

| | | | | |
|---|---|---|---|---|
| 197,933 A | * | 12/1877 | Harvey | 411/413 |
| 4,053,982 A | * | 10/1977 | Weissman | 433/225 |
| 4,662,806 A | * | 5/1987 | Reed | 411/2 |
| 4,863,383 A | * | 9/1989 | Grafelmann | 433/174 |
| 4,892,429 A | * | 1/1990 | Giannuzzi | 411/383 |
| RE33,901 E | * | 4/1992 | Shinjo | 411/387 |
| 5,415,507 A | * | 5/1995 | Janusz et al. | 411/5 |
| 5,928,236 A | * | 7/1999 | Augagneur et al. | 606/73 |
| 5,964,768 A | * | 10/1999 | Huebner | 606/73 |
| 6,102,913 A | * | 8/2000 | Jackson | 606/61 |
| 6,106,208 A | * | 8/2000 | Lin | 411/418 |
| 6,200,323 B1 | * | 3/2001 | Pierson, III | 606/102 |
| 6,261,040 B1 | * | 7/2001 | Reynolds et al. | 411/416 |
| 6,261,292 B1 | * | 7/2001 | Diebold et al. | 606/73 |

* cited by examiner

Primary Examiner—Pedro Philogene
Assistant Examiner—David A Bonderer
(74) Attorney, Agent, or Firm—Young & Thompson

(57) ABSTRACT

Device for securing bits of bone together, particularly small-sized bats of bone, for example bits of metatarsal head, in the form of a spindle including an elongate shank (1) followed, after a breakable region (2), by a fixator element (3) extending frustoconically to reduce in diameter in the direction of the anterior end (4), with a screw thread the pitch of which decreases progressively from the anterior end and of which the crests of the thread lie inside a coaxial geometric cylinder (D), the anterior end forming a self-drilling end.

10 Claims, 1 Drawing Sheet

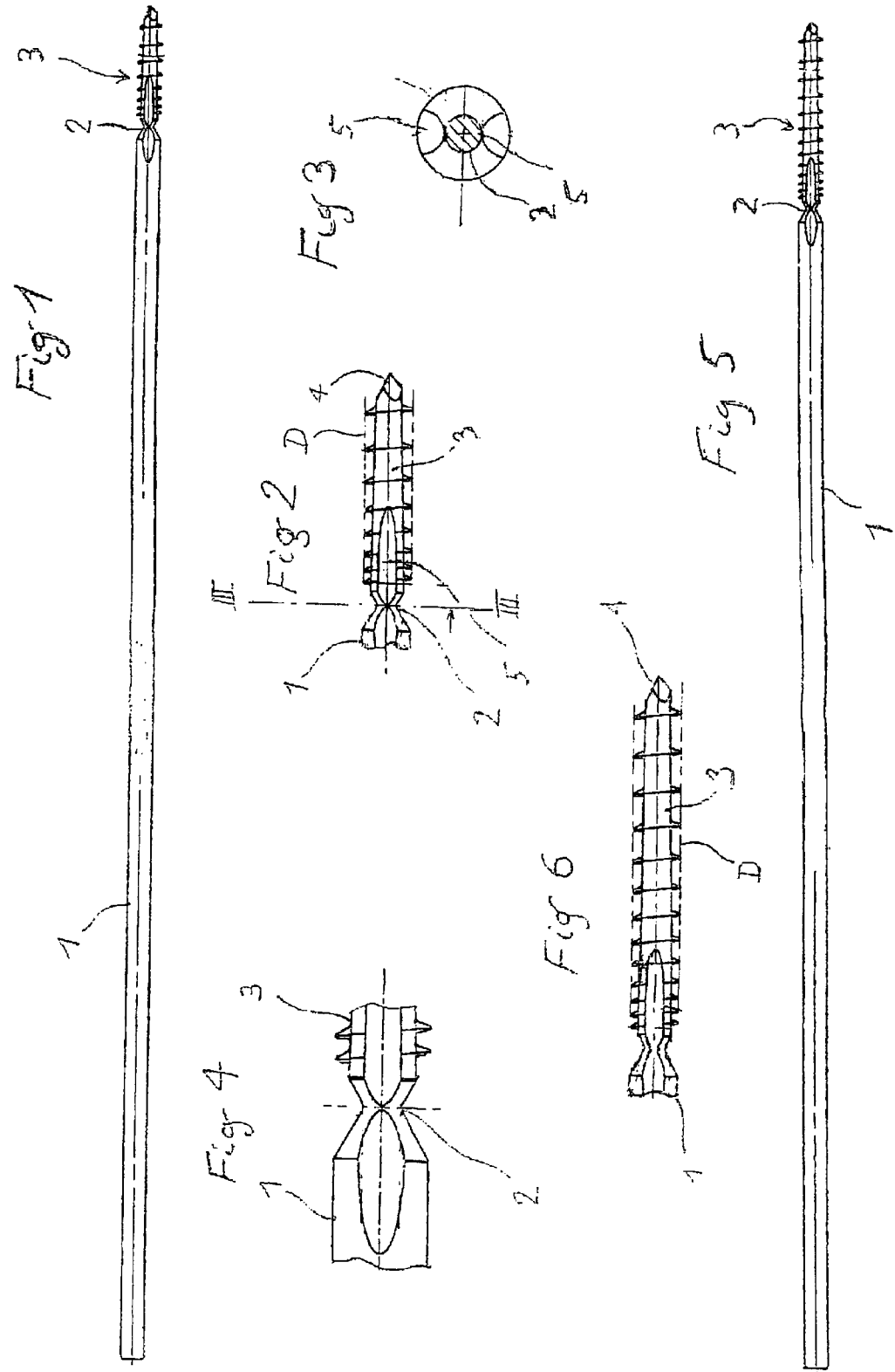

DEVICE FOR SECURING BITS OF BONE TOGETHER

BACKGROUND OF THE INVENTION

The present invention relates to a device for securing bits of bone together, such as, in particular, bits of metatarsal head, for example in the context of repair using the Weil osteotomy.

DESCRIPTION OF THE RELATED ART

The Weil osteotomy is an operation which consists in taking a line, on a metatarsal head, parallel to the sole of the foot and in shifting a bit backward, then in securing the bits of bone together.

To join small-sized bone fragments or elements together use is commonly made of surgical screws containing threaded portions intended to be screwed into the two bits of bone which are to be held together, and it is known practice for the screw threads present on such screws to be given different pitches so as to ensure firm anchorage and a compression effect that encourages the bone to take and encourages osteointegration.

These screws made, for example, of a biocompatible material, such as titanium, are difficult to handle accurately, particularly as a result of their small size. They often have a complex construction which increases their cost price. Finally, they entail the use of ancillaries, generally bulky and ill-suited to precisely checking the exact position of the screw set in place in the bone fragments.

SUMMARY OF THE INVENTION

The present invention sets out to overcome these drawbacks and to provide a device for securing bones together which is particularly easy to handle and to fit and which provides excellent consolidation.

The subject of the invention is a device for securing bits of bone together, particularly small-sized bits of bone, for example bits of metatarsal head, characterized in that it is in the form of a spindle comprising an elongate shank, followed, after a region in which the material is weakened, to allow it to be broken, by a fixator element, extending frustoconically so that it reduces in diameter in the direction of the free anterior end of the element, and, on this frustoconical surface, having a screw thread the pitch of which decreases progressively from said anterior end and of which the crests of the threads, the bottoms of which are formed by said frustoconical surface, lie inside a geometric cylinder coaxial with the axis of the spindle, said anterior end being beveled so as to form a self-drilling end, so as to allow it to be screwed self-tappingly into the bits of bone.

This results in a growing increase in the thread depth from the region of weakness toward the free anterior end.

The self-drilling end is preferably achieved by a point of the trocar type, formed, for example, of three inclined panels angularly offset by 120°.

As a preference, the shank of the spindle, which is connected to the fixator element proper by a region of weakness determining a breakable region, has a smooth or otherwise treated cylindrical surface to make it easier to hold in a rotary apparatus such as a drill.

The breakable part is advantageously produced in the form of a groove of roughly triangular cross section, the point of which determines a fairly acutely angled groove bottom, which facilitates breakage, by angular tilting, of the fixator element with respect to the shank, while at the same time being perfectly able to withstand the stresses generated as the fixator element is driven into the bits of bone.

In one preferred embodiment, the posterior part of the fixator element, which extends toward the region of weakness, has longitudinal grooves partially interrupting the threads in that region, so as to allow the introduction of corresponding fingers of a tool that allows, if need be the fixator element to be unscrewed by turning it in the opposite direction to the direction in which it is turned in order to drive it into the bits of bone.

The spindle according to the invention may thus be used to join and press together two fragments of bone after these have been respectively positioned by the surgeon, followed possibly by the drilling of a pre-hole with a spindle of smaller diameter and the introduction and compressive screwing-in of the spindle according to the invention into its final position, followed by breakage of the breakable region, and removal of the actual shank of the spindle.

In one advantageous embodiment it is possible, in order to drill the pre-hole, to use a threaded spindle of a smaller diameter, after which the spindle according to the invention is placed, this giving rise to the displacement of small volumes of bony substance between the threads, making osteointegration easier.

As a preference and according to the invention, a number of spindles according to the invention, having different dimensions in terms of the length and/or in terms of the thread crest diameter and/or in terms of the cone angle and/or in terms of the pitch are grouped together into a set.

As a preference, the spindles of one set differ in the length of the implantable fixator element, the thread crest diameter remaining unchanged.

The number of different sizes of spindle in a set or kit such as this is advantageously between 10 and 16, it being possible for the set to have one or more spindles in each size.

As a preference, the dimensions of the device according to the invention lie in the following ranges:
  length of the fixator element between the tip and the bottom of the breakable groove: 9 mm to 40 mm.
  cone angle of the fixator element: 0.75°±0.5°.
  mean diameter of the frustoconical surface: 1.2 mm.
  diameter of the geometric cylinder at the crest of the thread: 2 mm to 2.5 mm.
  variation in the thread pitch (from) 0.5 mm at the tip to 1.8 mm at the posterior end, it being possible for these values to vary by plus or minus 0.5 mm.

As a preference, the sections of the threads are roughly triangular with one face inclined toward the front of the fixator element and one face roughly perpendicular to the axis of the spindle toward the rear of the fixator element.

BRIEF DESCRIPTION OF THE DRAWINGS

Other features and advantages of the invention will become apparent on reading the following description, given by way of nonlimiting example and referring to the appended drawing, in which:

FIG. 1 depicts a view in elevation of a short spindle according to the invention, FIG. 2 depicts an enlarged view of the anterior end of the spindle, FIG. 3 depicts a view in section III—III and enlarged, of FIG. 2, FIG. 4 depicts an enlarged view, in elevation, of the part comprising the breakage region, FIG. 5 depicts a view similar to FIG. 1, for a long spindle, FIG. 6 depicts a view similar to FIG. 2 for this spindle.

DESCRIPTION OF THE PREFERRED EMBODIMENTS

Reference is made first of all to FIGS. 1 to 4.

These figures depict one form of embodiment of a spindle according to the invention, made of titanium grade TA6V, to ISO 5832/3 and 114 mm long. This spindle has a long cylindrical shank 1 ending at a triangular groove 2 forming a breakable region of weakness. The fixator element proper 3 extends from the bottom of this triangular groove 2.

That element, as can best be seen in FIG. 2, has a frustoconical shape with a small cone angle, and ends at the anterior end in a trocar point 4 formed of three beveled planes angularly offset by 120° about the longitudinal axis of the spindle.

From the anterior end, and more specifically from the rear of the tip 4, the spindle comprises a screw thread, the anterior thread flanks of which are inclined forward and inward, while the posterior flanks are roughly perpendicular to the axis. As can be seen in FIG. 2, the pitch of the screw thread diminishes progressively from the value of 1.76 mm to the value of 0.50 mm at the rear for the last turn of thread.

The groove-bottom diameter at the anterior end is 1 mm and is 1.4 mm at the posterior end, the mean diameter thus being 1.2 mm in the central region of the element 3. According to the invention, the crests of the threads all lie inside a geometric cylinder D having a diameter of 2 mm.

Thus the depth of the groove of the screw thread increases progressively toward the front, forming threads of increasing height so as to allow much improved anchorage which, combined with the progressive tightening provided by the variation in the pitch of the screw thread, considerably improves cohesion then osteointegration of the bone fragments brought together.

Two diametrically opposed longitudinal slots 5, the depth of which does not exceed the depths of the groove 3 are milled in the region of the groove 3, as can be seen in particular in FIG. 3. These slots extend partly into the anterior end of the shank 1 proper and extend over a large part of the posterior half of the element 3.

The spindle according to the invention is used as follows:

To perform the Weil osteotomy the surgeon brings together the two fragments of metatarsal bone that are to be joined, and holds them temporarily in the position that they are to occupy, using forceps. If necessary, at the site intended to take the element 3, he then drills a hole using a drill bit or a spindle, preferably threaded, the outside diameter of which is smaller than the diameter of the element 3. He then uses a rule to measure the length of the desired element 3. Having extracted the drilling spindle, he places the appropriately sized spindle 1 in the chuck of an apparatus such as a drill and screws the element 3 that forms the end of the spindle into the hole he drilled earlier. As the element 3 is driven in, the fragments of bone that are to be joined progressively find themselves pressed together. The surgeon then checks that the element 3 has been driven in by the desired amount, by checking the position of the bottom of the groove 3 against the bone cortex.

Having done that, he bends the shank 1 with respect to the element 3, which causes a clean break in the region 2, and the element 3 thus remains in its definitive position.

If the surgeon wishes to extract the element 3, he uses a chamfering cutter to uncover the periphery of the posterior end of the element 3, then uses an ancillary in the form of 8a screwdriver which at its anterior end has two longitudinally directed parallel fingers capable of fitting into the two grooves 5 of the posterior end of the element 3 in which they engage. Unscrewing can then be performed easily, the turning causing the fixator element 3 to be extracted.

Referring to FIG. 4, this depicts, using the same reference numerals, a spindle which has a longer part 3, the dimensions in terms of diameter remaining unchanged. The groove 5 preferably has a length identical to that of the groove 5 in FIG. 2, so that it no longer occupies most of the posterior part of the element 3.

What is claimed is:

1. Device for securing bits of bone together, particularly including small-sized bits of bone, for example bits of metatarsal head, characterized in that it is in the form of comprising:

a spindle having an longitudinal axis and comprising
an elongate shank (1) with a weakened region (2), the weakened region configured to allow the elongate shank to be broken,
a fixator element (3) following the weakened region, the fixator element having a frustonconical surface extending frustoconically so that the fixator element reduces in diameter in a direction of a free anterior end (4) of the fixator element, and,
a screw thread on the frustoconical surface,
the screw thread having
a pitch decreasing progressively from said anterior end and,
bottoms formed by said frustoconical surface,
crests which lie inside a geometric cylinder (D) coaxial with the axis of the spindle,
said anterior end (4) being beveled and forming a drilling end, so as to allow said anterior end to be screwed into the bits of bone, wherein
a posterior part of the fixator element (3) extending toward the weakened region (2) has longitudinal grooves (15) partially interrupting the threads in the weakened region, so as to allow the introduction of corresponding fingers of a tool that allows the fixator element to be unscrewed by turning the fixator element in an opposite direction to a direction in which the fixator element is turned for self-tapping.

2. Device according to claim 1, wherein, the weakened region is in the form of a groove (2) of roughly triangular cross section (4) with a point defining an acutely angled groove bottom, which groove facilitates breakage, by angular tilting, of the fixator element with respect to the shank, while at the same time being able to withstand stresses generated as the fixator element is driven into the bits of bone.

3. Device according to claim 2, wherein sections of the threads are roughly triangular with one face inclined toward a front of the fixator element and one face roughly perpendicular to the axis of the spindle toward a rear of the fixator element (3).

4. Device according to claim 1, wherein sections of the threads are roughly triangular with one face inclined toward a front of the fixator element and one face roughly perpendicular to the axis of the spindle toward a rear of the fixator element (3).

5. Device according to claim 1, wherein the sections of the threads are roughly triangular with one face inclined toward a front of the fixator element and one face roughly perpendicular to the axis of the spindle toward a rear of the fixator element (3).

6. Device according to claim 1, wherein
the device is one of a set of devices comprising a number of like devices,
dimensions of the fixator element (3) of each of the like devices varying as to at least one of length, screw thread crest diameter, cone angle, and pitch.

7. Device according to claim 6, wherein,
the like devices in the set have different lengths of fixator element (3), and
a diameter of a geometric cylinder in which the crests of the thread lie remains constant.

8. Device according to claim 1, wherein,
the device is one of a set of devices comprising
a number of like devices,
the like devices in the set have different lengths of fixator element (3),
a diameter of a geometric cylinder in which the crests of the thread lie remains constant.

9. Device for securing bits of bone together, comprising:
a. spindle having an axis, the spindle comprising
an elongate shank (1) with a weakened breakable region, to allow the shank to be broken,
a fixator element (3) following the breakable region, the fixator element having a frustoconical surface extending frustoconically and reducing in diameter in the a direction of a free anterior end (4) of the fixator element, and
on this frustoconical surface, having a screw thread,
a pitch of which screw thread decreases progressively from said anterior end and,
bottoms of which threads are formed by said frustoconical surface,
crests of the threads laying inside a geometric cylinder (D) coaxial with the axis of the spindle,
said anterior end (4) being beveled so as to form a drilling end, so as to allow the anterior end to be screwed into the bits of bone, wherein,
the breakable region is in the form of a groove (2) of roughly triangular cross section (4), the point of which groove determines an acutely angled groove bottom, which groove facilitates breakage of the breakable region, by angular tilting, of the fixator element with respect to the shank, the breakable region being able to withstand stresses generated as the fixator element is driven into the bits of bone, and
a posterior part of the fixator element (3), which extends toward the breakable region (2), has longitudinal grooves (15) partially interrupting threads in the breakable region, so as to allow the introduction of corresponding fingers of a tool that allows the fixator element to be unscrewed by turning in an opposite direction to a direction turned for self-tapping.

10. Device according to claim 9, wherein,
the devices is one of a set of devices having different lengths of fixator element (3), and an equal diameter of a geometric cylinder in which the crests of the thread lie.

* * * * *